United States Patent
Lim et al.

(10) Patent No.: US 9,846,166 B2
(45) Date of Patent: Dec. 19, 2017

(54) BIOSENSOR USING CELL THAT EXPRESSES CHEMOSENSORY RECEPTOR THAT CAN DETECT SUGAR, AND ALZHEIMER'S DISEASE DIAGNOSTIC APPARATUS COMPRISING SAME

(71) Applicant: Kyungpook National University Industry-Academic Cooperation Foundation, Buk-gu, Daegu (KR)

(72) Inventors: Jeong Ok Lim, Daegu (KR); Won Ju Cho, Seoul (KR); Jeung Soo Huh, Gyeongsangbuk-do (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 69 days.

(21) Appl. No.: 14/901,558

(22) PCT Filed: Oct. 4, 2013

(86) PCT No.: PCT/KR2013/008881
§ 371 (c)(1),
(2) Date: Dec. 28, 2015

(87) PCT Pub. No.: WO2014/208820
PCT Pub. Date: Dec. 31, 2014

(65) Prior Publication Data
US 2016/0139152 A1    May 19, 2016

(30) Foreign Application Priority Data

Jun. 24, 2013 (KR) .......................... 10-2013-0072476

(51) Int. Cl.
*G01N 27/327* (2006.01)
*G01N 33/68* (2006.01)
(Continued)

(52) U.S. Cl.
CPC ..... *G01N 33/6896* (2013.01); *G01N 27/3275* (2013.01); *G01N 27/4145* (2013.01);
(Continued)

(58) Field of Classification Search
CPC ............. G01N 27/414; G01N 27/4145; G01N 33/6896
See application file for complete search history.

(56) References Cited

U.S. PATENT DOCUMENTS

2012/0245854 A1    9/2012    Haick et al.

FOREIGN PATENT DOCUMENTS

| JP | 2012-225762 A | 11/2012 |
|---|---|---|
| KR | 100113639 B1 | 4/1996 |

(Continued)

OTHER PUBLICATIONS

Sakata et al., "Continuous Monitoring of Electrical Activity of Pancreatic ε-Cells Using Semiconductor-Based Biosensing Devices," Japanese Journal of Applied Physics 50 (2011) 020216.*

(Continued)

*Primary Examiner* — Alexander Noguerola
(74) *Attorney, Agent, or Firm* — Thompson Coburn LLP

(57) ABSTRACT

The present invention relates to a biosensor that uses a cell that expresses a chemosensory receptor that can detect sugar, and an Alzheimer's disease diagnostic apparatus comprising the same. The biosensor and the Alzheimer's disease diagnostic apparatus of the present invention can sensitively detect a particular sugar in a sample, more inexpensively and more quickly, by fixing a drosophila cell having an over-expressed target sensory receptor protein on (Continued)

the cell surface through genetic engineering, and can thereby be efficaciously used for diagnosing Alzheimer's disease.

8 Claims, 11 Drawing Sheets

(51) Int. Cl.
    *G01N 27/414*      (2006.01)
    *G01N 33/66*      (2006.01)
    *G01N 33/543*      (2006.01)

(52) U.S. Cl.
    CPC ......... *G01N 33/5438* (2013.01); *G01N 33/66* (2013.01); *G01N 2333/43573* (2013.01); *G01N 2400/00* (2013.01); *G01N 2800/2821* (2013.01)

(56) References Cited

FOREIGN PATENT DOCUMENTS

| | | |
|---|---|---|
| KR | 20110119513 A | 11/2011 |
| KR | 20120091842 A | 8/2012 |

OTHER PUBLICATIONS

Prabhulkar et al., "Microbiosensor for Alzheimer's Disease Diagnostics: Detection of Amyloid Beta Biomarkers", J. Neurochem. Jul. 2012; 122(2); 374-381.*

JP 2012-225762 A English language translation obtained from the JPO on Apr. 29, 2017.*

Schuller et al., "Field-effect saccharide sensing using AlGaN/GaN heterostructures and boronic acid based chemical receptors," Sensors and Actuators B 160 (2011) 1078-1081.*

* cited by examiner

BIOSENSOR USING CELL THAT EXPRESSES CHEMOSENSORY RECEPTOR THAT CAN DETECT SUGAR, AND ALZHEIMER'S DISEASE DIAGNOSTIC APPARATUS COMPRISING SAME

TECHNICAL FIELD

The present invention relates to biosensors using cells that express chemosensory receptors that can detect sugar, and Alzheimer's disease diagnostic apparatus comprising the same.

BACKGROUND ART

Alzheimer's disease (AD) is a degenerative brain disease which occurs in 11% of the older population aged 60 and older, and the number of patients increases rapidly as the population ages. AD has a significant impact on quality of life and economic losses of medical expenses, etc. (WHO Report, 2010). The treatment methods and drugs for AD relate to slowing down the progression of the disease and alleviate its symptoms, rather than fundamentally preventing the disease. There, it is very necessary and significant to alleviate patients' pain and reduce social costs incurred in relation with the disease, by providing appropriate treatment to the patients through early diagnosis. As current diagnostic methods, gene tests, cerebrospinal collection, PET or MRI, etc., are used. However, these methods are not only expensive but also invasive, which is burden to patients. Also, the representative AD biomarker known up to now is beta amyloid, which is aggregated in the brain and is a direct cause of onset AD. Meanwhile, recently, the research on other biomarkers is actively proceeding using advanced analysis apparatus.

Meanwhile, there are many concerns in biosensors which can quickly and simultaneously detect artificial aptamers, modified proteins, toxins, etc., in addition to naturally occurring molecules including naturally occurring DNA, RNA, protein, virus, or pathogen. The development of biosensor technologies helps promoting various medical fields, such as discovery of drugs, detection of genetic mutants, and evaluation on treatment effect of genes.

Biosensors using field effect transistors (FETs), which were first invented in the 1970s, sense a change in environment through a change in current between two places with respect to one reference place, using a source electrode, a drain electrode, and a gate electrode of the FET. Upon reviewing its principles, electrochemical potential difference in the interface between a solution and a sensing membrane varies depending on ion concentration in the solution. The change in potential difference generates a change in voltage in an effective gate region caused by a change in threshold voltage, and this change modifies channel conductivity, which causes a change in current of the drain electrode. The change in concentration of a particular ion present in the solution can be detected by measuring the change in current of the drain electrode, and the formation of an ion sensing membrane selectively sensitive to the particular ion can lead to the preparation of a sensor capable of sensing various ions. Biosensors using the FET can mount numerous sensing elements on one chip, thereby allowing multidimensionalization by arranging same type of multiple sensors and multifunctionalization by arranging different types of multiple sensors. Also, the biosensors can be intellectualized by mounting intellectual circuits, or mounting relevant circuits and devices, to be systematized. There, they draw attention as high-tech sensors.

Drosophila has well developed olfactory and gustatory sensory receptors, its genetic information is well known, and chemo sensory receptors present in cell surface sensitively react with particular smell or taste. There, when drosophila cells are used as a sensing substance, the sensitivity and selectivity may be optimized.

Accordingly, the present inventors analyzed the saliva of patients using GC-MS for searching for noninvasive AD biomarkers and found sugar components which are substances variously and specifically appearing in patients with brain disorders, to select the substances as a new biomarker for AD, and prepared a drosophila cell based ion-sensitive field effect transistor (ISFET) biosensor. Further, the present inventors confirmed that the biosensor sensitively reacts with trehalose, which is one of the sugar components, and in the saliva of the patients with AD, thereby completing the present invention.

SUMMARY OF INVENTION

It is an object of the present invention to provide a biosensor comprising a cell expressing a chemosensory receptor sensitive to sugar; and a field effect transistor in which the cell is fixed.

It is another object of the present invention to provide an Alzheimer's disease diagnostic apparatus, comprising a sensing unit comprising a biosensor in which a cell expressing a chemosensory receptor sensitive to sugar is fixed; a reference unit for comparing a change in voltage or current with the biosensor, comprising a field effect transistor in which a cell non-expressing a chemosensory receptor sensitive to sugar is fixed; and a controlling unit for comparing a difference in voltage or current between the sensing unit and the reference unit.

Accordingly, the object of the present invention is to provide a biosensor comprising a cell expressing a chemosensory receptor sensitive to sugar; and a field effect transistor in which the cell is fixed.

Also, the present invention provides an Alzheimer's disease diagnostic apparatus, comprising a sensing unit comprising a biosensor in which a cell expressing a chemosensory receptor sensitive to sugar is fixed; a reference unit for comparing a change in voltage or current with the biosensor, comprising a field effect transistor in which a cell non-expressing a chemosensory receptor sensitive to sugar is fixed; and a controlling unit comparing a difference in voltage or current between the sensing unit and the reference unit.

The biosensor and the Alzheimer's disease diagnostic apparatus using the same of the present invention can sensitively detect a particular sugar in a sample, more inexpensively and more quickly, by fixing a drosophila cell having an over-expressed target sensory receptor protein on the cell surface through genetic engineering, and can thereby be efficaciously used for diagnosing Alzheimer's disease.

BEST MODE FOR CARRYING OUT THE INVENTION

The present invention provides a biosensor comprising a cell expressing a chemosensory receptor which detects sugar; and a field effect transistor in which the cell is fixed.

Hereinafter, the present invention is described in detail.

The cell of the present invention may be derived from a drosophila cell. The drosophila cell may be used by transfecting Drosophila Schenider 2 (S2) cells which cannot detect sugar with a gene of a chemosensory receptor. A method typically known in the art may be used as the method of gene transfection. The chemosensory receptor may be preferably a Gr5a protein that sensitively detects sugar, but is not limited thereto.

The field effect transistor may be preferably an ion-sensitive field-effect transistor.

Figure 3:
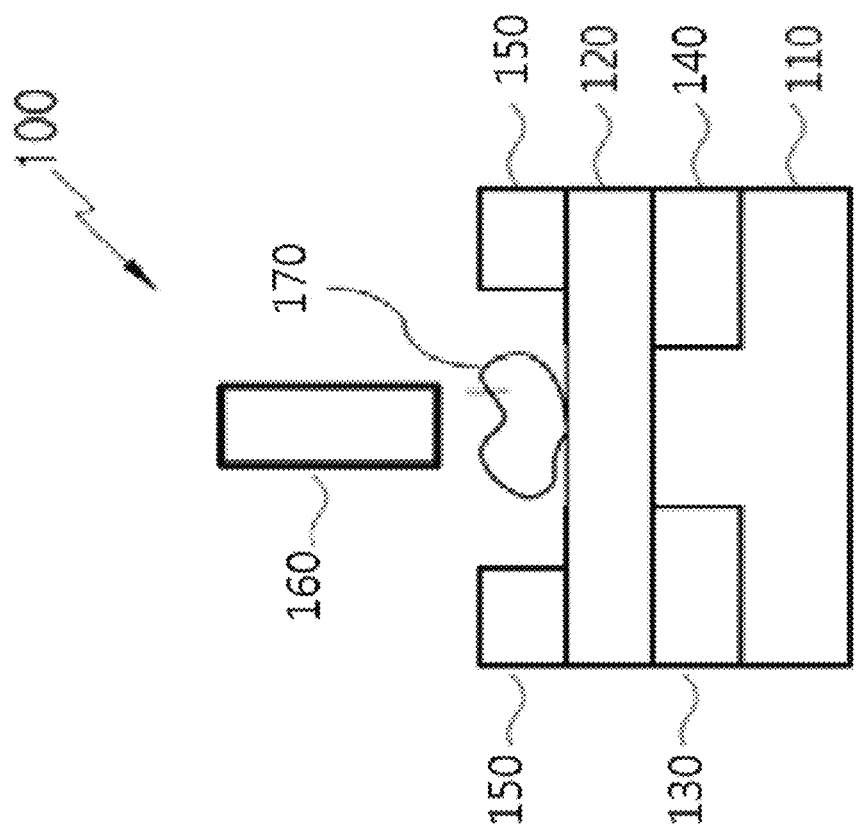
FIG. 3 is a view illustrating a biosensor according to the present invention.

As illustrated in FIG. 3, a biosensor 100 of the present invention includes a silicon layer 110, an oxide layer 120, a drain electrode 130, and a source electrode 140.

The silicon layer 110 may be located in a substrate (not shown in the drawings), and the substrate may be prepared with a material selected from the group consisting of silicon, germanium, glass, metal, plastic, oxide, and a mixture thereof.

The silicon layer 110 may be formed of graphene or silicon, and preferably silicon. The silicon layer 110 may be used as an electrode by depositing or probing a metallic material capable of forming an ohmic contact to the silicon layer 110 and forming a contact layer, in order to effectively apply a voltage.

Figure 4:
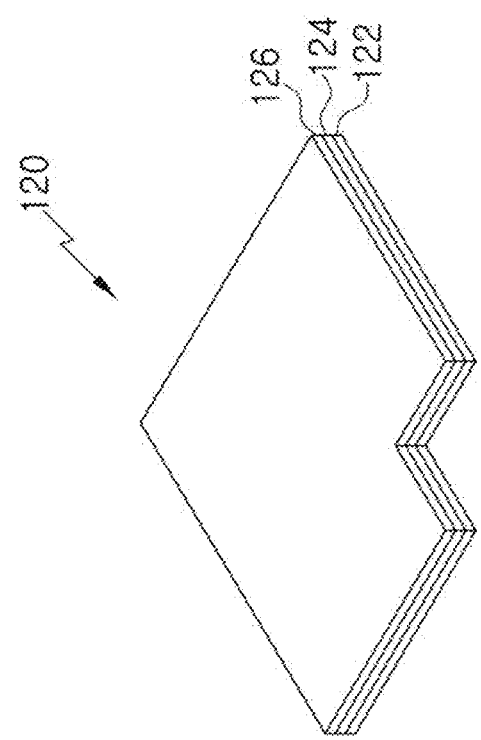
FIG. 4 is a view illustrating the structure of an oxide layer of a biosensor according to the present invention.

The oxide layer 120, which serves as a membrane sensing hydrogen ion concentration, may act as a gate insulating layer which regulates electrical conductivity formed in a channel layer. The oxide layer 120 may have a thickness of preferably 10 nm to 1000 nm. As illustrated in FIG. 4, the oxide layer 120 may include a silicon dioxide layer 122, a hafnium oxide layer 124, and an aluminum oxide layer 126. The silicon dioxide layer of the present invention has a thickness of preferably 3 to 7 nm, and more preferably 5 nm. Further, the hafnium oxide layer 124 may have a thickness of preferably 5 to 10 nm, and more preferably 7.8 nm.

Further, the aluminum oxide layer 126 may have a thickness of preferably 10 to 16 nm, and more preferably 13.8 nm.

The source electrode 130 and the drain electrode 140 may be used as electrodes by depositing or probing a metallic material capable of forming an ohmic contact and forming a contact layer. The source electrode and the drain electrode may be formed of a material typically well-known in the art.

The cell of the present invention overexpressing the chemosensory receptor which detects sugar may be mainly fixed in the oxide layer 120. When a biological sample, etc. to be reacted is introduced into an electrolyte 170, the sample reacts with a sugar component including trehalose or sugar of the chemosensory receptor which the cell expresses, to generate an ion. The generated ion causes an electrochemical potential difference between the oxide layer (sensing membrane) and the cell. The potential difference varies depending on the presence and concentration of the sugar component in the biological sample. The change in the potential difference leads to a change in threshold voltage ($V_t$), and the change in threshold voltage may cause a change in effective gate voltage ($V_{gd}$). The conductance of the channel layer varies in proportional to the gate voltage by the field effect generated therefrom, and the presence and concentration of sugar component may be detected by measuring the change in drain electrode current ($I_{ds}$).

Also, when the change occurs in the concentration of sugar component in the electrolyte 170 at a constant drain voltage ($V_{ds}$), the gate voltage varies in order to maintain a constant drain electrode current ($I_{ds}$). The presence of sugar component and the change in concentration thereof may be detected by measuring the change amount.

Further, the biosensor of the present invention may further include a wall structure 150 to store the electrolyte 170 solution and a reference electrode 160 that is a reference of voltage measurement.

The sugar of the present invention may include all types of sugar, preferably trehalose or sugar.

Figure 5:
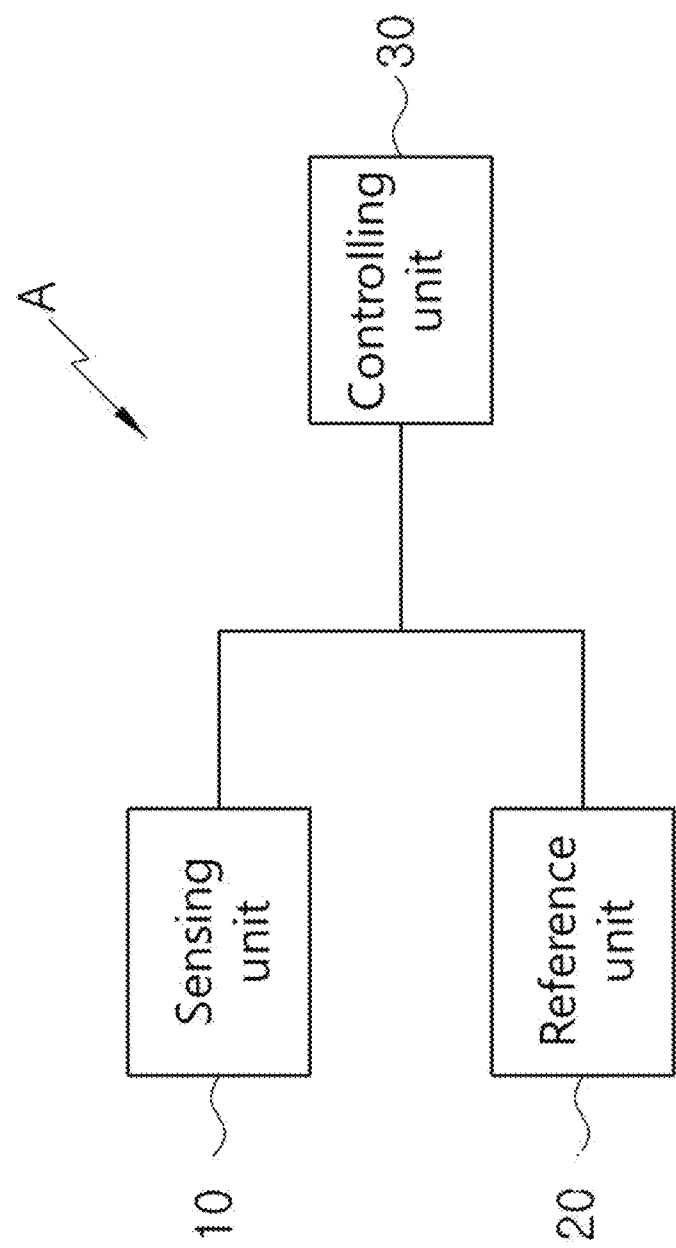
FIG. 5 is a schematic view illustrating an embodiment of an Alzheimer's disease diagnostic apparatus according to the present invention.

As illustrated in FIG. 5, the Alzheimer's disease diagnostic apparatus A according to the present invention includes a sensing unit 10, a reference unit 20, and a controlling unit 30.

The sensing unit 10 includes the biosensor 100 in which a cell expressing a chemosensory receptor which detects sugar is fixed. When a biological sample including the saliva of a patient with Alzheimer's disease is introduced into the sensing unit, a change in drain current or gate voltage of the biosensor occurs. When a biological sample including the saliva of a normal person with no Alzheimer's disease is introduced into the sensing unit, the drain current or gate voltage of the biosensor does not significantly vary.

The reference unit 20 includes the biosensor 100 in which a cell non-expressing a chemo sensory receptor sensitive to sugar is fixed. When a biological sample including the saliva of a normal person or a patient with Alzheimer's disease is introduced into the reference unit, the drain current or gate voltage of the biosensor does not significantly vary.

The controlling unit 30 compares the difference in the drain current or gate voltage between the sensing unit and the reference unit, and can diagnose Alzheimer's disease when there is a difference in current or voltage between the sensing unit 10 and the reference unit 20.

Embodiments for Carrying of the Invention

Hereinafter, the present invention will be described in detail with reference to embodiments. The following embodiments are for illustrative purposes only, and the present invention is not limited to the scope of the embodiments.

EXAMPLE 1

Development of Biomarker for Alzheimer's Disease 1-1. Collection of Saliva from Patients with Alzheimer's Disease Before collecting the saliva of patients with Alzheimer's disease, the patients have fasted for 4 hours or more. Then, 1 ml of saliva was put into 1.7 ml sterilized vial treated with 2% of sodium azide, which is a preservative. The saliva was centrifuged at 1500 rpm for 5 minutes to separate a supernatant, and put into a new vial to be kept at 4° C. For a long-term storage, the saliva was kept at −80° C.

1-2. GC-MS Analysis of Saliva of Patients with Alzheimer's Disease

Each saliva of 53 patients with Alzheimer's disease, and a control group including 23 patients with Parkinson's disease, 7 patients with mild cognitive impairment, and 12 normal persons, 101 persons in total, was analyzed with a gas chromatograph mass spectrometer (GS/MS, Agilent: column-HP-5, Inlet temp 250° C., Column flow 1.0 ml/min, Mas range 50-600 m/z, Fiber 65 µm PDMS/DVB pink/plain). The qualitative and quantitative analysis were conducted on substances, and the search for a biomarker was performed through data mining. The result is shown in FIG. 1.

Figure 1:
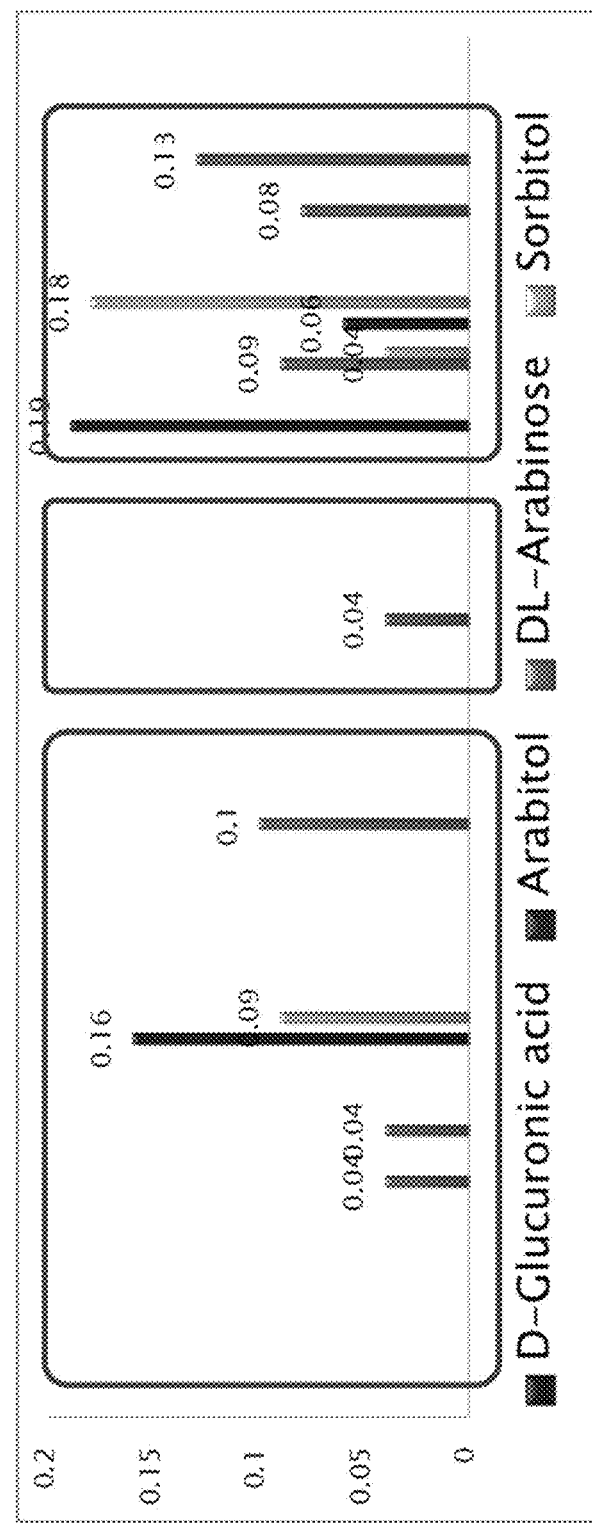
FIG. 1 is a view illustrating a result of analyzing sugar components and amounts thereof included in the saliva of a patient with Alzheimer's disease.

As shown in FIG. 1, it was found that a large amount of sugar components was detected in the patients with Alzheimer's disease. From this, it was confirmed that these components may be used as a biomarker for Alzheimer's disease.

EXAMPLE 2

Preparation of Drosophila Cell Expressing Gr5a Protein which is Sensitive to Sugar Components A cell line expressing Gr5a, which is one of drosophila gustatory receptors, was established with Drosophila Expression System (Invitrogen) using Drosophila Schneider 2 (S2) cells that cannot detect sugar (http://tools.invitrogen.com/content/sfs/manuals/des_man.pdf).

After cloning Gr5a cDNA into a pAC vector, the S2 cell line was co-transfected with 2 µg of the cloned plasmid and 200 ng of pCoHygro which is a selection vector resistant to hygromycin, using polyethylenimine (PEI) in a Schneider medium (Invitrogen) containing no serum. A stable cell line expressing Gr5a was established by culturing in a medium containing hygromycin every 4 days, at least 6 times. The process for preparing the cell line expressing Gr5a and the result thereof were shown in FIG. 2.

Figure 2:
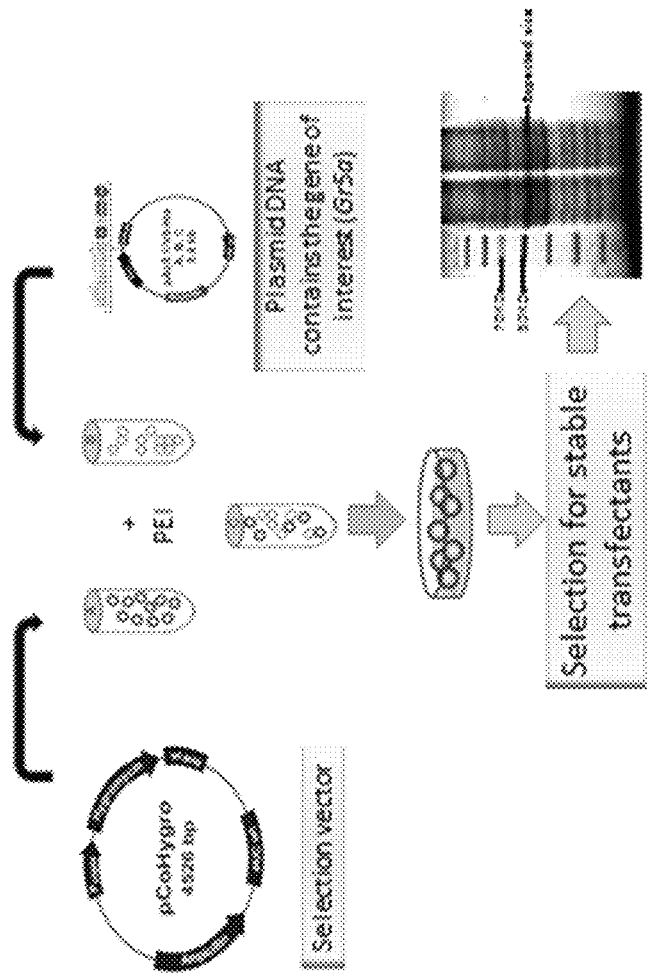
FIG. 2 is a view illustrating a process of transfecting a drosophila cell with a chemo sensory receptor Gr5a and a result confirming the transfection.

As shown in FIG. 2, it was confirmed that the S2 cells were transfected with the Gr5a gene.

EXPRESSION 3

Preparation of Biosensor Based on Ion-Sensitive Field Effect Transistor (ISFET)

A high concentration of a polycrystalline silicon thin film was deposited on a p-type silicon substrate through a low pressure chemical vapor deposition (LPCVD) vacuum equipment, and a source electrode and a drain electrode were formed spaced away from each other using lithographic and dry etching processes. An oxide layer was formed of a silicon dioxide ($SiO_2$) layer, a hafnium oxide ($HfO_2$) layer located on the silicon dioxide layer, and an aluminum oxide ($Al_2O_3$) layer located on the hafnium oxide layer, on the silicon layer. Rapid thermal treatment (at 850° C. for 30 seconds) was conducted under $N_2/O_2$ gas atmosphere, in order to activate the source electrode, the drain electrode, and the oxide layer, successively. After the rapid thermal treatment, a metal electrode was deposited by e-beam deposition. Thereafter, a wall structure was constructed with polydimethylsiloxane (PDMS), and an electrolyte was put into the wall structure, to prepare an ISFET based biosensor.

FIG. 3 illustrates the prepared ISFET based biosensor. FIG. 4 illustrates the structure of the oxide layer. FIG. 5 illustrates the schematic view illustrating an Alzheimer's disease diagnostic apparatus prepared based thereon.

EXAMPLE 4

Evaluation on Properties of Biosensor of the Present Invention

A substance improving the properties of the sensing membrane (oxide layer), which is the most significant element of the biosensor of the present invention, was synthesized, and an ISFET biosensor was prepared with a newly developed sensing membrane, to sensitively detect a signal between a cell and a reactant. Thereby, the transfer properties of the element were evaluated by analysis of sensitivity and stability properties and electronic properties of the element of the biosensor.

Figure 6:
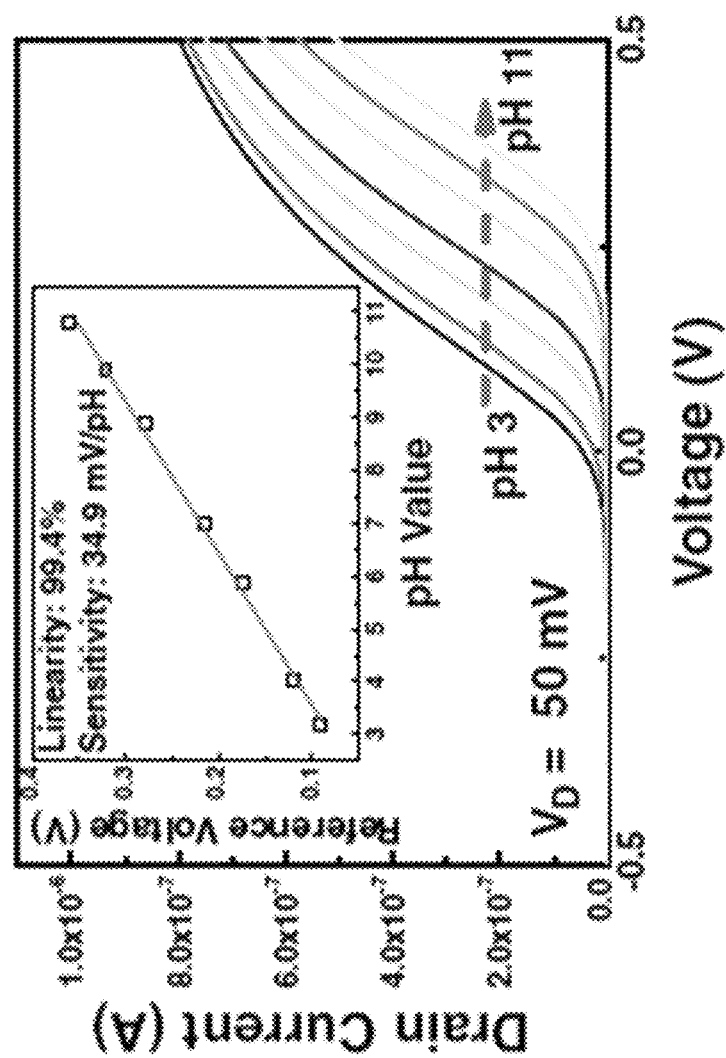
FIGS. 6 and 7 are views evaluating characteristics of a sensing membrane (oxide layer) of a biosensor according to the present invention.
Figure 7:
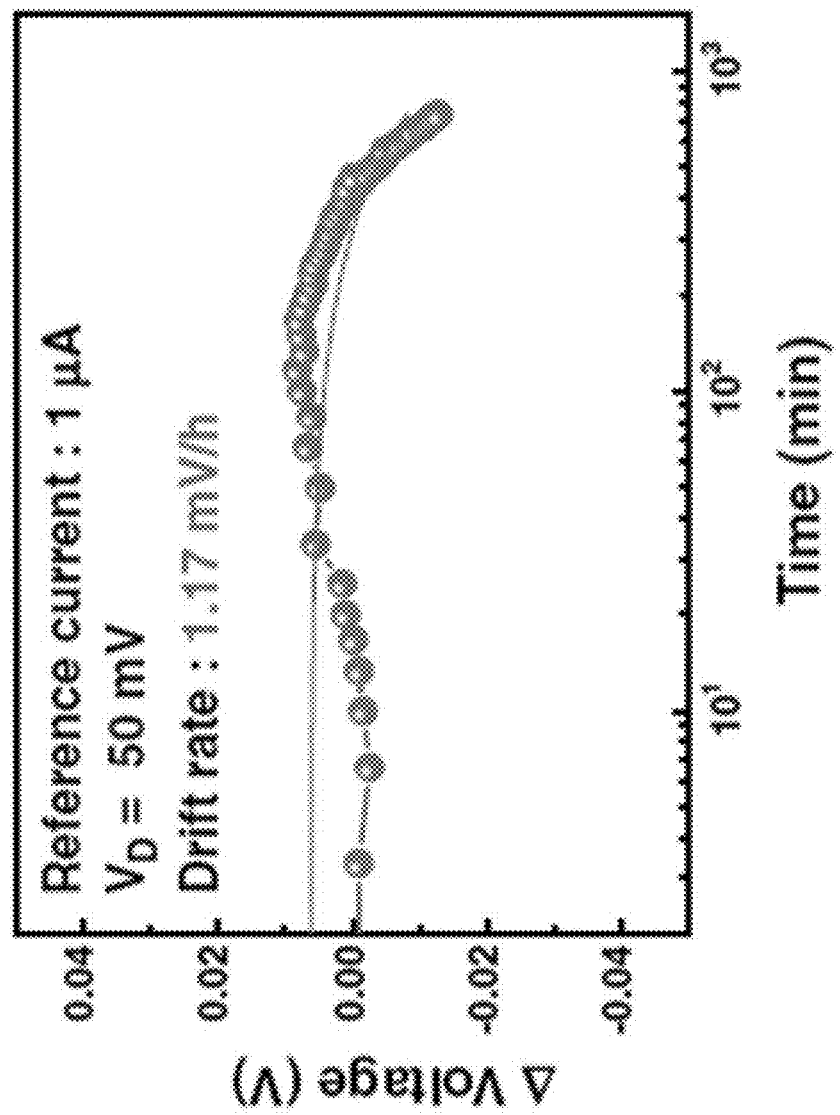

The results are shown in FIGS. 6 and 7.

As shown in FIGS. 6 and 7, it was found that the drift rate of the sensing member in the pH buffer is 1.17 mV/h, the sensitivity is 34.9 mV/pH, and the linearity is 99.4%. From this, it was confirmed that the sensing member is very stable.

EXAMPLE 5

Patients with Alzheimer's Disease using Biosensor of the Present Invention

Figure 8:
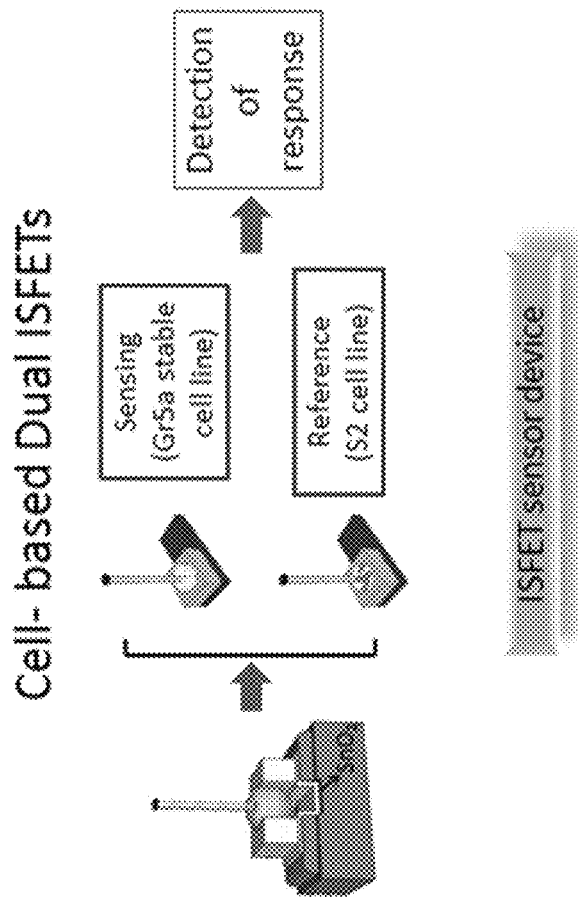
FIG. 8 is a view briefly illustrating a cell-based dual ISFET according to the present invention.
Figure 9:
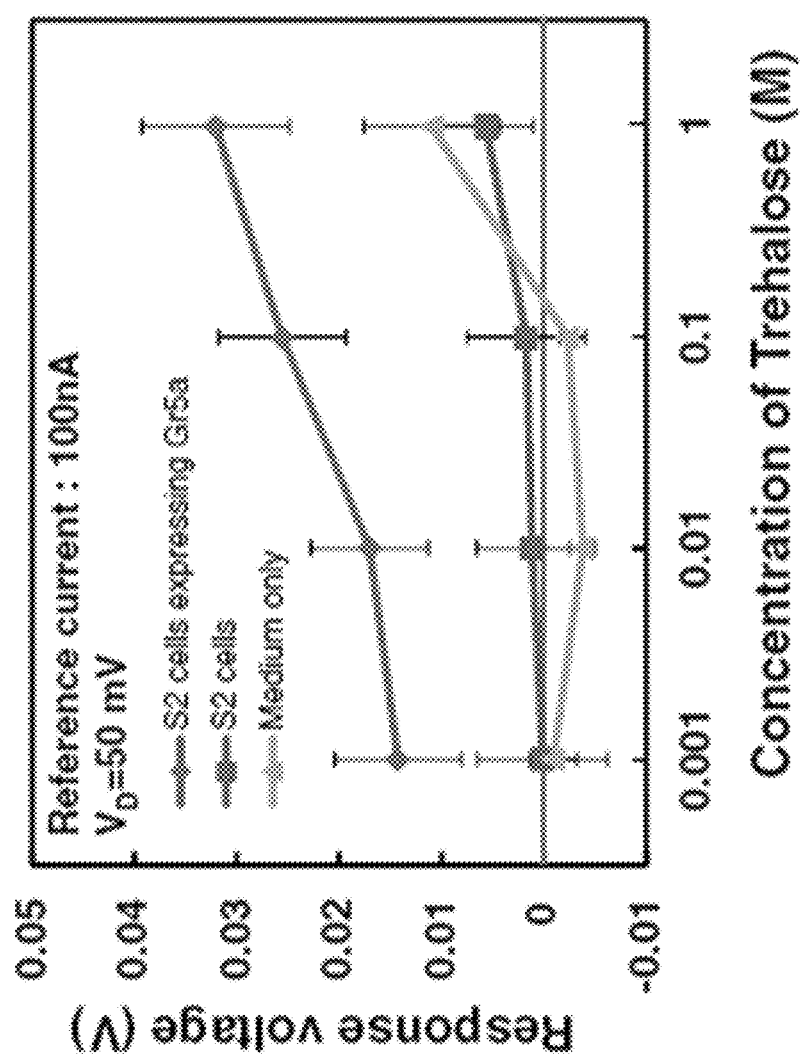
FIG. 9 is a view illustrating a change in voltage depending on the type of cell fixed in a biosensor and the concentration of trehalose introduced.
Figure 10:
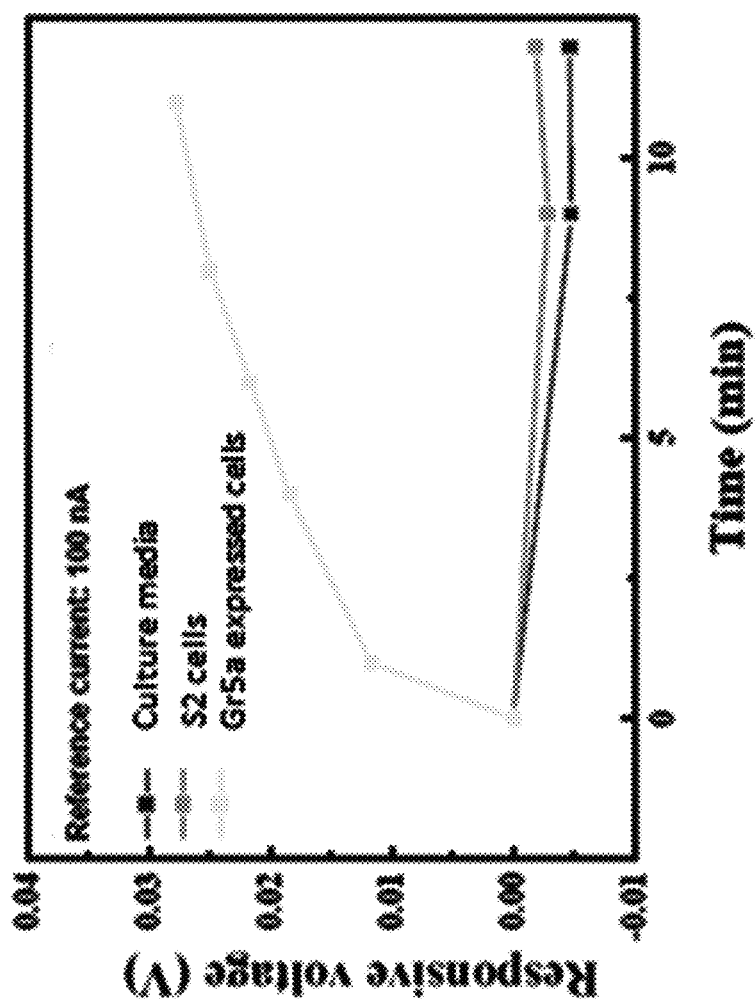
FIG. 10 is a view illustrating a change in voltage depending on the type of cell fixed in a biosensor, when the saliva of a patient with Alzheimer's disease is introduced into the biosensor.
Figure 11:
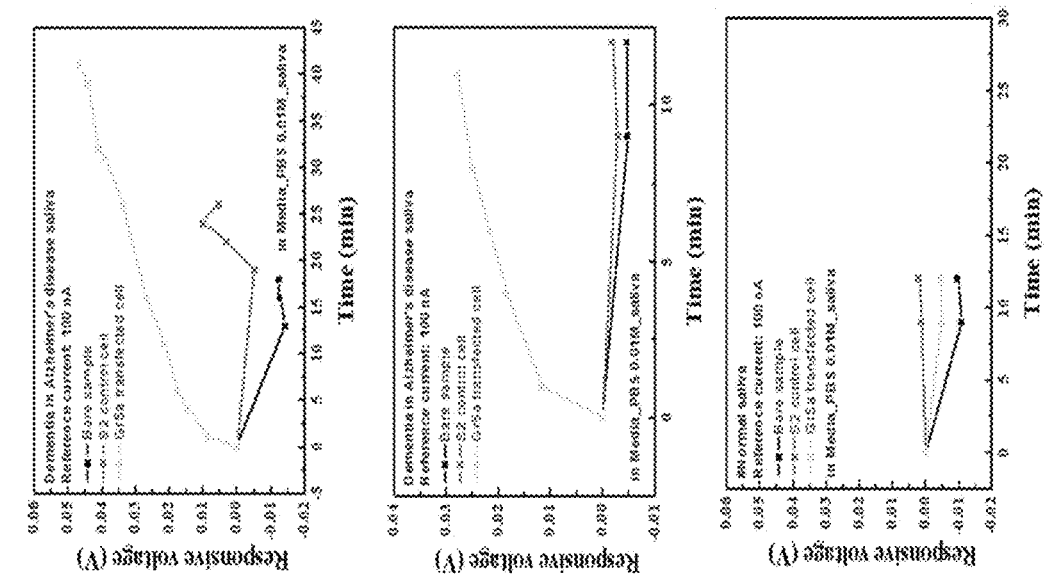
FIG. 11 is a view illustrating a change in voltage depending on the type of cell fixed in a biosensor, when the saliva of patients A and B with Alzheimer's disease or of a normal person C is introduced into the biosensor.

A pair ISFET structure was developed capable of sensing by distinguishing the experimental group from the control group, as shown in FIG. 8. FIG. 9 illustrates a change in voltage of the pair ISFET depending on the concentration of trehalose, which is a type of sugar. FIG. 10 illustrates a change in voltage of the pair ISFET (sensing unit which is a biosensor in which drosophila cells overexpressing Gr5a are fixed; reference unit which is a biosensor in which S2 cells or cell culture media are fixed), when the saliva of the patients with Alzheimer's disease is introduced into the pair ISFET. FIG. 11 illustrates a change in voltage, when the saliva of the patients with Alzheimer's disease or normal persons is introduced into the pair ISFET.

As shown in FIG. 9, it was confirmed that when trehalose is introduced into the biosensor (sensing unit) in which a drosophila cell line expressing Gr5a sensitive to sugar is fixed, a voltage remarkably increases as the concentration of trehalose introduced increases. By comparison, it was confirmed that when trehalose is treated to the biosensor (reference unit) in which S2 cells or general culture media are fixed, a voltage changes little although the concentration of trehalose introduced increases.

As shown in FIG. 10, it was confirmed that when the saliva of the patients with Alzheimer's disease is introduced into the sensing unit, the voltage increases, and that when the saliva of the patients with Alzheimer's disease is introduced into the reference unit, the voltage does not change.

As shown in FIG. 11, it was confirmed that when the saliva of the patients with Alzheimer's disease (FIG. 11(A) and 11(B)) is introduced into the sensing unit or the reference unit, the voltage significantly changes in the sensing unit, whereas the voltage does not change in the reference unit, and that when the saliva of normal persons (FIG. 11(C)) was introduced into the sensing unit or the reference unit, the voltage does not change both in the sensing unit and the reference unit.

Accordingly, it was confirmed that Alzheimer's disease can be diagnosed using the pair ISFET.

EXPLANATION ON REFERENCE NUMERALS

A: Alzheimer's disease diagnostic apparatus
10: Sensing unit
20: Reference unit
30: Controlling unit
100: Biosensor
110: Silicon layer
120: Oxide layer
122: Silicon dioxide layer
124: Hafnium oxide layer
126: Aluminum oxide layer
130: Drain electrode
140: Source electrode
150: Wall structure
160: Reference electrode
170: Electrolyte solution

What is claimed is:

1. A biosensor comprising:
    a cell expressing a chemosensory receptor sensitive to sugar, wherein the chemosensory receptor is a Gr5a protein of a drosophila; and
    a field effect transistor in which the cell is fixed.

2. The biosensor of claim 1, wherein the cell is a drosophila cell overexpressing the Gr5a protein, transfected with a Gr5a gene.

3. The biosensor of claim 1, wherein the field effect transistor is an ion-sensitive field effect transistor.

4. The biosensor of claim 3, wherein the ion-sensitive field effect transistor comprises a silicon layer, a source electrode, a drain electrode and an oxide layer; wherein the source electrode and drain electrode are located separately on the silicon layer, wherein the oxide layer is located on the silicon layer, the source electrode and drain electrode, and wherein the cell expressing a chemosensory receptor sensitive to sugar is fixed on the oxide layer.

5. The biosensor of claim 4, wherein the oxide layer is composed of a silicon dioxide ($SiO_2$) layer, a hafnium oxide ($HfO_2$) layer located on the silicon dioxide layer, and an aluminum oxide ($Al_2O_3$) layer located on the hafnium oxide layer.

6. The biosensor of claim 1, wherein the cell is a drosophila cell overexpressing a Gr5a protein; wherein the field effect transistor is an ion-sensitive field effect transistor; wherein the ion-sensitive field effect transistor comprises a silicon layer, a source electrode, a drain electrode and an oxide layer, wherein the source electrode and drain electrode are located separately on the silicon layer, wherein the oxide layer is located on the silicon layer, the source electrode and drain electrode, and wherein the cell expressing a chemosensory receptor sensitive to sugar is fixed on the oxide layer; and wherein the oxide layer is composed of a silicon dioxide ($SiO_2$) layer, a hafnium oxide ($HfO_2$)layer located on the silicon dioxide layer, and an aluminum oxide ($Al_2O_3$)layer located on the hafnium oxide layer.

7. The biosensor of claim 1, wherein the sugar is trehalose.

8. An Alzheimer's disease diagnostic apparatus, comprising:
    a sensing unit comprising the biosensor of claim 1;
    a reference unit for comparing a change in voltage or current with the biosensor, comprising a field effect transistor in which a cell non-expressing a chemosensory receptor sensitive to sugar is fixed; and
    a controlling unit for comparing a difference in voltage or current between the sensing unit and the reference unit.

* * * * *